US008257430B2

(12) United States Patent  (10) Patent No.: US 8,257,430 B2
Mead  (45) Date of Patent: Sep. 4, 2012

(54) INTERCONNECTED LEG EXTENSIONS FOR AN ENDOLUMINAL PROSTHESIS

(75) Inventor: Jason A. Mead, Plainfield, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1505 days.

(21) Appl. No.: 11/014,669

(22) Filed: Dec. 16, 2004

(65) Prior Publication Data

US 2005/0177222 A1   Aug. 11, 2005

Related U.S. Application Data

(60) Provisional application No. 60/530,388, filed on Dec. 17, 2003.

(51) Int. Cl.
*A61F 2/82* (2006.01)
*A61F 2/84* (2006.01)
(52) U.S. Cl. ........................ 623/1.35; 623/1.11
(58) Field of Classification Search ........ 623/1.11–1.54; 606/194, 200
See application file for complete search history.

(56) References Cited

U.S. PATENT DOCUMENTS

| | | | |
|---|---|---|---|
| 4,994,071 A | 2/1991 | MacGregor | |
| 5,104,404 A * | 4/1992 | Wolff | 623/1.16 |
| 5,135,536 A | 8/1992 | Hillstead | |
| 5,489,295 A | 2/1996 | Piplani et al. | |
| 5,507,769 A | 4/1996 | Marin et al. | |
| 5,562,724 A | 10/1996 | Vorwerk | |
| 5,575,817 A | 11/1996 | Martin | |
| 5,591,195 A | 1/1997 | Taheri | |
| 5,609,627 A | 3/1997 | Goicoechea et al. | |
| 5,632,763 A | 5/1997 | Glastra | |
| 5,676,697 A | 10/1997 | McDonald | |
| 5,683,451 A | 11/1997 | Lenker | |
| 5,709,713 A | 1/1998 | Evans | |
| 5,713,917 A | 2/1998 | Leonhardt | |
| 5,755,773 A | 5/1998 | Evans et al. | |
| 5,769,882 A | 6/1998 | Fogarty | |
| 5,782,906 A | 7/1998 | Marshall et al. | |
| 5,824,040 A * | 10/1998 | Cox et al. | 623/1.35 |
| 5,893,887 A | 4/1999 | Jayaraman | |
| 5,904,713 A * | 5/1999 | Leschinsky | 623/1.35 |
| 5,911,732 A | 6/1999 | Hojeibane | |
| 5,961,548 A | 10/1999 | Shmulewitz | |

(Continued)

FOREIGN PATENT DOCUMENTS

EP   0 880 948 A1   12/1998

(Continued)

OTHER PUBLICATIONS

Kubota, Y. et al.; "Bilateral Internal Biliary Drainage of Hilar Cholangiocarcinoma with Modified Gianturco Z Stents Inserted via a Single Percutaneous Tract;" 1993 JVIR 4:605-610.

(Continued)

*Primary Examiner* — Kathleen Sonnett
(74) *Attorney, Agent, or Firm* — Brinks Hofer Gilson & Lione (57) ABSTRACT

An endoluminal prosthesis includes two stent grafts with a flexible bridge extending between and connected to the stent grafts. The prosthesis can be part of a prosthesis assembly for treatment of branched vascular systems and can function as an interconnected leg extension prosthesis in combination with a main bifurcated prosthesis. In treating abdominal aortic aneurysms, the prosthesis can be deployed within both iliac arteries.

9 Claims, 11 Drawing Sheets

U.S. PATENT DOCUMENTS

| | | | |
|---|---|---|---|
| 6,022,359 A * | 2/2000 | Frantzen | 606/108 |
| 6,033,434 A | 3/2000 | Borghi | |
| 6,039,749 A | 3/2000 | Marin et al. | |
| 6,051,020 A | 4/2000 | Goicoechea et al. | |
| 6,056,775 A | 5/2000 | Borghi et al. | |
| 6,068,655 A | 5/2000 | Seguin et al. | |
| 6,077,297 A | 6/2000 | Robinson et al. | |
| 6,093,203 A | 7/2000 | Uflacker | |
| 6,102,938 A | 8/2000 | Evans et al. | |
| 6,110,198 A | 8/2000 | Fogarty | |
| 6,117,167 A | 9/2000 | Goicoechea et al. | |
| 6,129,756 A | 10/2000 | Kugler et al. | |
| 6,143,002 A | 11/2000 | Vietmeier | |
| 6,183,509 B1 | 2/2001 | Dibie | |
| 6,197,049 B1 | 3/2001 | Shaolian et al. | |
| 6,200,339 B1 * | 3/2001 | Leschinsky et al. | 623/1.35 |
| 6,245,102 B1 | 6/2001 | Jayaraman | |
| 6,283,991 B1 | 9/2001 | Cox | |
| 6,299,634 B1 | 10/2001 | Bergeron | |
| 6,306,164 B1 | 10/2001 | Kujawski | |
| 6,325,819 B1 | 12/2001 | Pavcnik et al. | |
| 6,344,056 B1 * | 2/2002 | Dehdashtian | 623/1.35 |
| 6,355,061 B1 | 3/2002 | Quiachon et al. | |
| 6,368,345 B1 | 4/2002 | Dehdashtian et al. | |
| 6,395,022 B1 | 5/2002 | Piplani et al. | |
| 6,409,757 B1 | 6/2002 | Trout, III | |
| 6,416,542 B1 | 7/2002 | Marcade et al. | |
| 6,436,134 B2 | 8/2002 | Richter et al. | |
| 6,454,796 B1 * | 9/2002 | Barkman et al. | 623/1.35 |
| 6,464,720 B2 | 10/2002 | Boatman | |
| 6,475,208 B2 | 11/2002 | Mauch | |
| 6,478,813 B1 | 11/2002 | Keith et al. | |
| 6,485,510 B1 | 11/2002 | Camrud et al. | |
| 6,508,836 B2 | 1/2003 | Wilson et al. | |
| 6,524,335 B1 | 2/2003 | Hartley et al. | |
| 6,524,336 B1 | 2/2003 | Papazolgou et al. | |
| RE38,146 E | 6/2003 | Palmaz et al. | |
| 6,576,009 B2 | 6/2003 | Ryan | |
| 6,585,753 B2 | 7/2003 | Eder et al. | |
| 6,602,225 B2 | 8/2003 | Eidenschink et al. | |
| 6,602,281 B1 * | 8/2003 | Klein | 623/1.15 |
| 6,666,883 B1 | 12/2003 | Seguin et al. | |
| 6,673,107 B1 * | 1/2004 | Brandt et al. | 623/1.35 |
| 6,695,875 B2 | 2/2004 | Stelter | |
| 6,695,877 B2 | 2/2004 | Brucker et al. | |
| 6,827,735 B2 | 12/2004 | Greenberg | |
| 6,860,900 B2 * | 3/2005 | Clerc et al. | 623/1.35 |
| 6,878,161 B2 | 4/2005 | Lenker | |
| 7,131,991 B2 | 11/2006 | Zarins | |
| 2001/0027338 A1 | 10/2001 | Greenberg | |
| 2002/0042644 A1 | 4/2002 | Greenhalgh | |
| 2002/0120233 A1 | 8/2002 | Eidenschink et al. | |
| 2002/0156517 A1 | 10/2002 | Perouse | |
| 2002/0156521 A1 | 10/2002 | Ryan et al. | |
| 2002/0156522 A1 | 10/2002 | Ivancev et al. | |
| 2002/0198585 A1 | 12/2002 | Wisselink | |
| 2002/0198587 A1 | 12/2002 | Greenberg et al. | |
| 2003/0097169 A1 | 5/2003 | Brucker et al. | |
| 2003/0149473 A1 | 8/2003 | Chouinard et al. | |
| 2003/0158594 A1 | 8/2003 | Kang et al. | |
| 2003/0199967 A1 | 10/2003 | Hartley | |
| 2003/0220682 A1 | 11/2003 | Kujawski | |
| 2004/0054404 A1 | 3/2004 | Wilson et al. | |
| 2004/0082990 A1 | 4/2004 | Hartley | |
| 2004/0111148 A1 * | 6/2004 | Goodson | 623/1.16 |
| 2004/0153147 A1 | 8/2004 | Mathis | |
| 2004/0167616 A1 | 8/2004 | Camrud | |
| 2004/0176833 A1 | 9/2004 | Pavcnik | |
| 2004/0210306 A1 | 10/2004 | Quijano et al. | |
| 2004/0230287 A1 | 11/2004 | Hartley | |
| 2004/0243221 A1 | 12/2004 | Fawzi et al. | |
| 2005/0234542 A1 | 10/2005 | Melsheimer | |
| 2006/0089704 A1 | 4/2006 | Douglas | |
| 2006/0161244 A1 | 7/2006 | Seguin | |
| 2006/0178726 A1 | 8/2006 | Douglas | |

FOREIGN PATENT DOCUMENTS

| | | |
|---|---|---|
| WO | WO 98/07389 | 2/1998 |
| WO | WO 98/44870 | 10/1998 |
| WO | WO 98/53761 | 12/1998 |
| WO | WO 02/067815 A1 | 9/2002 |
| WO | WO 03/065933 A1 | 8/2003 |
| WO | WO 03/082153 A2 | 10/2003 |
| WO | WO 2004-100836 A1 | 11/2004 |

OTHER PUBLICATIONS

US 6,413,270, 07/2002, Thornton et al. (withdrawn)

* cited by examiner

INTERCONNECTED LEG EXTENSIONS FOR AN ENDOLUMINAL PROSTHESIS

RELATED APPLICATIONS

The present patent document claims the benefit of the filing date under 35 U.S.C. §119(e) of Provisional U.S. Patent Application Ser. No. 60/530,388, filed Dec. 17, 2003, which is hereby incorporated by reference.

TECHNICAL FIELD

This invention relates to prostheses for implantation within the human or animal body for the repair of damaged lumens such as blood vessels.

BACKGROUND

The functional vessels of human and animal bodies, such as blood vessels and ducts, occasionally weaken or even rupture. For example, in the aortic artery, the vascular wall can weaken or tear, resulting in dangerous conditions such as aneurysm and dissection. Treatment of such conditions can be performed by implanting a prosthesis within the vascular system using minimally invasive surgical procedures. An endoluminal prosthesis typically includes one or more stents affixed to graft material and is delivered to the treatment site by endovascular insertion. Once the endoluminal prosthesis is radially enlarged, it should remain in place indefinitely by self-attachment to the vessel wall, acting as a substitute vessel for the flow of blood or other fluids.

Treatment of vascular conditions near a branch point with an endoluminal prosthesis can present a number of difficulties. A single, straight section of a tubular prosthesis may not be able to span the aneurysm or dissection and still maintain sufficient contact with healthy vascular tissue to secure the prosthesis and to prevent endoleaks. For example, most abdominal aortic aneurysms occur at or near the iliac bifurcation, and treatment with an endoluminal prosthesis requires the presence of prosthesis material in the main aorta and in the iliac branch arteries (Dietrich, E. B. *J. Invasive Cardiol.* 13(5):383-390, 2001). Typically, an endoluminal prosthesis for use near a bifurcation will have a main lumen body, for placement within the aorta, and two branch lumens extending from the main lumen body into the branch arteries.

A simple approach to bifurcated prostheses from a materials perspective is to use a single piece prosthesis. Such unitary structures have a main tubular body and pre-formed leg extensions. The seamless structure provided by this configuration can minimize the probability of leakage within the prosthesis. However, the constrained geometry of branched vasculature makes it extremely difficult to deliver such a large structure to the treatment site. For example, in treating aortic aneurysms, the deployment of a leg extension down the contralateral iliac artery is especially problematic.

A more common alternative to the single piece approach is the use of a modular system. In these systems, one or both of the leg extensions can be attached to a main tubular body to provide the final prosthesis. Examples of modular systems are described in PCT Patent Application Publication WO98/53761 and in U.S. patent application Publication 2002/0198587 A1, which are incorporated herein by reference. Although the delivery of modular systems is less difficult due to the smaller sizes of the individual components, it can still be a complex and time-consuming process to make the precise connections between the body and one or both legs. The difficulty and risk of the treatment procedure can also increase when there are more individual parts to insert, align, and deploy. Possible complications with modular systems include the occurrence of endoleaks, due to imperfect seals between the body and a leg component, and the separation of the legs from the main prosthesis body over time.

BRIEF SUMMARY

In one aspect of the invention, there is an endoluminal prosthesis, comprising a first stent graft; a second stent graft; and a flexible bridge extending between and connected to the first and second stent grafts.

In another aspect of the invention, there is an endoluminal prosthesis assembly, comprising a bifurcated prosthesis comprising a main tubular body having a single proximal opening and two distal openings; and an interconnected extension prosthesis comprising a first stent graft, a second stent graft, and a flexible bridge extending between and connected to the first and second stent grafts.

These aspects may further include an endoluminal prosthesis wherein the first stent graft comprises a plurality of self-expanding stents; wherein the second stent graft comprises a plurality of self-expanding stents; wherein the flexible bridge comprises a wire; wherein the flexible bridge comprises a partial stent; wherein the first and second stent grafts each comprise a stent adjacent the flexible bridge, and the flexible bridge is integral with at least one of the stents; wherein the flexible bridge is integral with both of the stents; and wherein the flexible bridge is integral with one of the stents and is affixed to the other stent. These aspects may further include an endoluminal prosthesis wherein the first and second stent grafts each comprise a stent affixed to the flexible bridge; wherein the first stent graft and the second stent graft each comprise a terminal opening and a central opening, the central openings adjacent to and on opposite ends of the flexible bridge; wherein the flexible bridge is bent at an acute angle when the prosthesis is deployed in a patient; wherein each of the first and second stent grafts comprise an internal stent at the central opening and an internal stent at the terminal opening; wherein the first stent graft further comprises at least one external stent between the central opening and the terminal opening; and wherein the second stent graft further comprises at least one external stent between the central opening and the terminal opening.

These aspects may further include an endoluminal prosthesis assembly wherein the interconnected extension prosthesis is sized and configured to engage the two distal openings of a bifurcated stent graft; wherein the bifurcated stent graft comprises a self-expanding stent attached to and extending from the proximal opening; wherein the bifurcated stent graft comprises a shorter stent graft leg between the main tubular body and one of the distal openings and a longer stent graft leg between the main tubular body and the other distal opening; and wherein the first stent graft is longer than the second stent graft, and wherein the first stent graft is sized and configured to engage the distal opening of the shorter stent graft leg and the second stent graft is sized and configured to engage the distal opening of the longer stent graft leg.

In yet another aspect of the invention, there is a method of treating an aortic aneurysm, comprising inserting into the aortic artery a bifurcated stent graft comprising a main tubular body having a single proximal opening, a first distal opening and a second distal opening; inserting at least a portion of an interconnected extension prosthesis into a first iliac artery, through the first distal opening and into the main tubular body; wherein the interconnected extension prosthesis is in a compressed state and comprises a first stent graft, a second stent graft and a flexible bridge extending between and connected to the first and second stent grafts; inserting at least a portion of the first stent graft through the second distal opening and into a second iliac artery; and allowing the interconnected extension prosthesis to expand to an expanded state such that the first stent graft sealingly engages the second distal opening and the second stent graft sealingly enages the first distal opening.

DETAILED DESCRIPTION

The present invention relates to an endoluminal prosthesis having leg extensions that are interconnected. The prosthesis includes two stent graft sections separated by a flexible bridge section. The stent graft sections are interconnected by the flexible bridge and can coordinate with a bifurcated prosthesis to form leg portions of an endoluminal prosthesis assembly. In the treatment of an aortic aneurysm, the prosthesis can be delivered through one iliac artery, into a main bifurcated prosthesis, and into the other iliac artery.

Throughout this specification, when discussing the application of this invention to the aorta, the term distal with respect to a prosthesis is intended to refer to the end of the prosthesis furthest away in the direction of blood flow from the heart, and the term proximal is intended to mean the end of the prosthesis that, when implanted, would be nearest to the heart.

The term "prosthesis" means any replacement for a body part or for a function of that body part; or any device that enhances or adds functionality to a physiological system.

The term "endoluminal" describes objects that are found or can be placed inside a lumen or space in the human or animal body. This includes lumens such as blood vessels, parts of the gastrointestinal tract, ducts such as bile ducts, parts of the respiratory system, etc. "Endoluminal prosthesis" thus describes a prosthesis that can be placed inside one of these lumens.

The term "graft" means a generally cannular or tubular member which acts as an artificial vessel. A graft by itself or with the addition of other elements can be an endoluminal prosthesis.

The term "stent" means any device or structure that adds rigidity, expansion force or support to a prosthesis. Typically, a stent has a tubular shape when used for endoluminal applications. The term "stent graft" means a stent that has been sewn, sutured, or otherwise connected to graft material. The term "partial stent" means a stent that has does not form a complete tubular shape, and is typically configured as a stent that has been divided along its axis or parallel to its axis.

Figure 1:
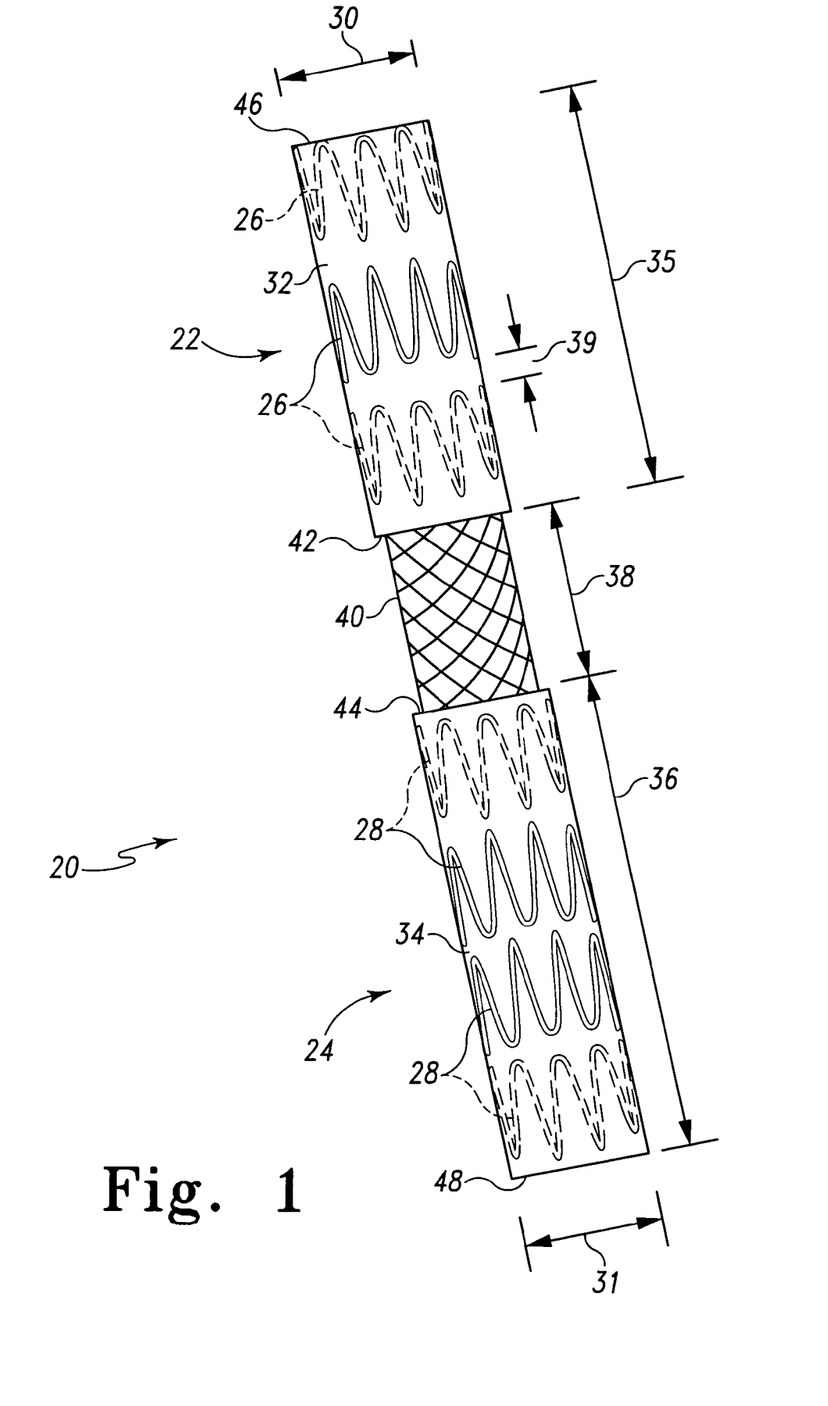
FIG. 1 shows an interconnected leg extension prosthesis.

Referring to FIG. 1, an example of an interconnected leg extension prosthesis 20 contains two tubular stent graft sections 22 and 24 connected by a flexible bridge 40. Each stent graft section contains at least one stent 26 or 28 attached to a biocompatible graft material 32 or 34. Each stent graft section has a central opening 42 or 44 near the flexible bridge and a terminal opening 46 or 48 away from the flexible bridge at the ends of the prosthesis. Each end of the flexible bridge is irreversibly attached to one of the stent graft sections at a central opening.

The graft material covering the stent or stents of each stent graft section is a biocompatible material. Preferably the biocompatible material is in the form of a fabric that is impermeable to liquids, including blood or other physiological fluids. Examples of biocompatible materials include polyesters, such as poly(ethylene terephthalate), and fluorinated polymers, such as polytetrafluoroethylene (PTFE) and expanded PTFE. Examples of biocompatible polyesters include DACRON (DUPONT, Wilmington, Del.) and TWILLWEAVE MICREL (VASCUTEK, Renfrewshire, Scotland). Examples of biocompatible materials also include extracellular matrix (ECM) materials, such as a purified collagen-based matrix derived from submucosa tissue. Examples of ECM materials include pericardium, stomach submucosa, liver basement membrane, urinary bladder submucosa, tissue mucosa, and dura mater. A specific example of an ECM material is small intestinal submucosa (SIS), such as is described in U.S. Pat. No. 6,206,931, which is incorporated herein by reference.

The graft material may be made of a single material, or it may be a blend, weave, laminate or composite of two or more materials. The graft material may also include other additives, such as plasticizers, compatibilizers, surface modifiers, biological materials such as peptides and enzymes, and therapeutic agents such as drugs or other medicaments. The particular graft material on each stent graft section may be the same, or the materials may be different. A single piece of graft material may be used, such that a portion of graft material spans the distance between the central openings.

The graft material for each stent graft section is secured to one or more stents. For example, standard surgical suturing techniques can be used to secure the graft material to a stent. A stent can be positioned on the interior of the tubular graft material, or it can be positioned on the exterior of the graft material. A stent can also be secured to one of the openings of the tubular graft material such that the stent extends from the material. A stent extending from the graft material can be secured to the interior and/or the exterior of the material. In another example, a stent can be sandwiched between two layers of graft material, and this stent may also be secured by sutures. Examples of suture material include PROLENE® (5-0).

Stents may have a wide variety of configurations and may be balloon-expandable or self-expanding. Typically, stents have a circular cross-section when fully expanded, so as to conform to the generally circular cross-section of a body lumen. For example, the stents used in the stent graft sections may be discrete stents having a zig-zag configuration in which straight struts are set at angles to each other and are connected by acute bends. The struts are thus connected into an endless loop, forming a generally tubular structure. Discrete zig-zag stents are also referred to as Gianturco stents or Z-stents. A specific example of a Z-stent is the Z-STENT available from COOK, INC. (Bloomington, Ind.). In another example, the stents may contain individual stent segments that are connected to provide an elongated, flexible stent. The individual stent segments can have a variety of configurations, including the zig-zag configuration. A specific example of a connected zig-zag stent is the ZILVER™ stent available from COOK, INC.

Stents may be made of any rigid biocompatible material, such as metal, plastic or ceramic. Preferably the stents are made of a metal, such as stainless steel, nitinol, and other biocompatible alloys. Stents may be equipped with one or more barbs to secure the prosthesis to the vessel wall or to another component of the prosthesis. If the stent is secured to the graft material by suturing, the sutures may be positioned along struts and/or at bends within the stent. For stents having a zig-zag configuration, it may be desirable to employ two sutures at each bend of the stent to further increase the stability of the connection, as described in Australian Provisional Patent Application No. 2002950951, which is incorporated herein by reference.

Figure 2A:
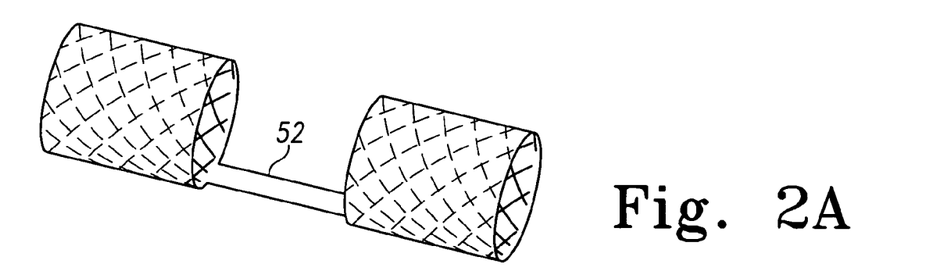
FIGS. 2A-2E show examples of interconnected leg extension prostheses having varying flexible bridge configurations.
Figure 2B:
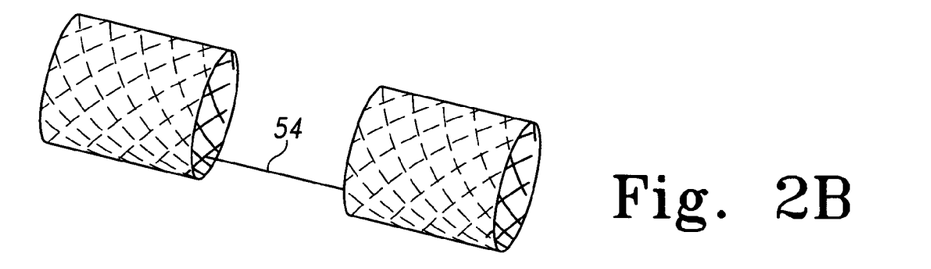
Figure 2C:
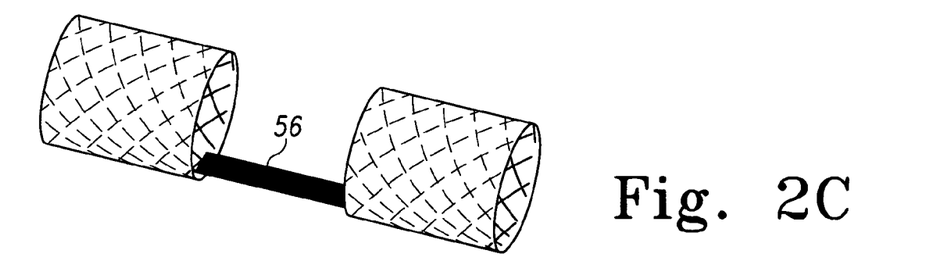
Figure 2D:
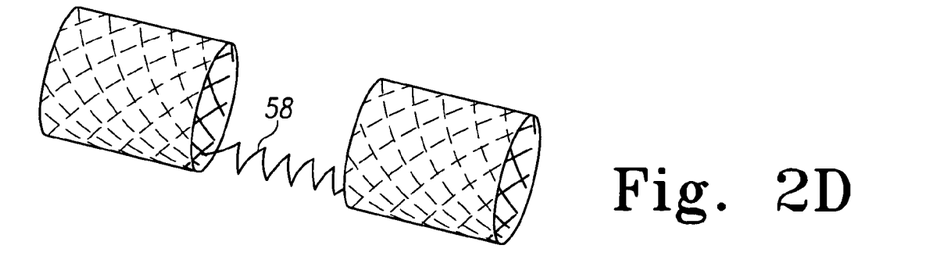
Figure 2E:
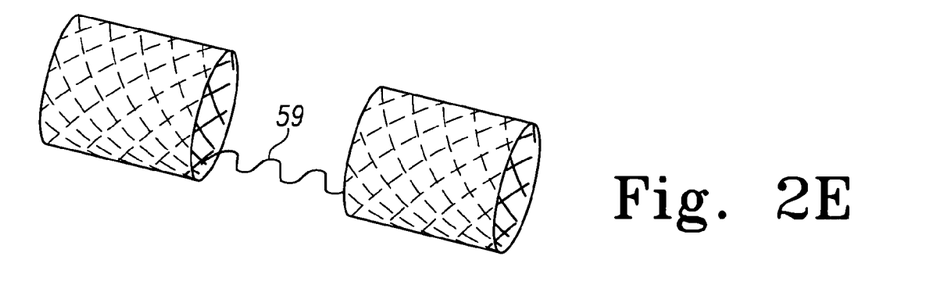

The flexible bridge can have a variety of configurations and serves to retain the stent graft sections within a minimum distance of each other. Referring to FIG. 2A, the flexible bridge may be a piece of graft material 52 that is sutured to or integral with the graft materials of each of the stent graft sections. Preferably the flexible bridge is made of a material such as metal, plastic or ceramic such that it has some rigidity but can still be bent into an acute angle. For example, referring to FIGS. 2B and 2C, the flexible bridge may be a portion of metal, plastic or ceramic configured as a wire 54 or a ribbon 56. Referring to FIGS. 2B through 2E, a flexible bridge configured as a wire or ribbon may form a relatively linear connection between the stent graft sections, or may have a more flexible shape, such as a zig-zag (58) or sinusoidal (59) shape.

Figure 3:
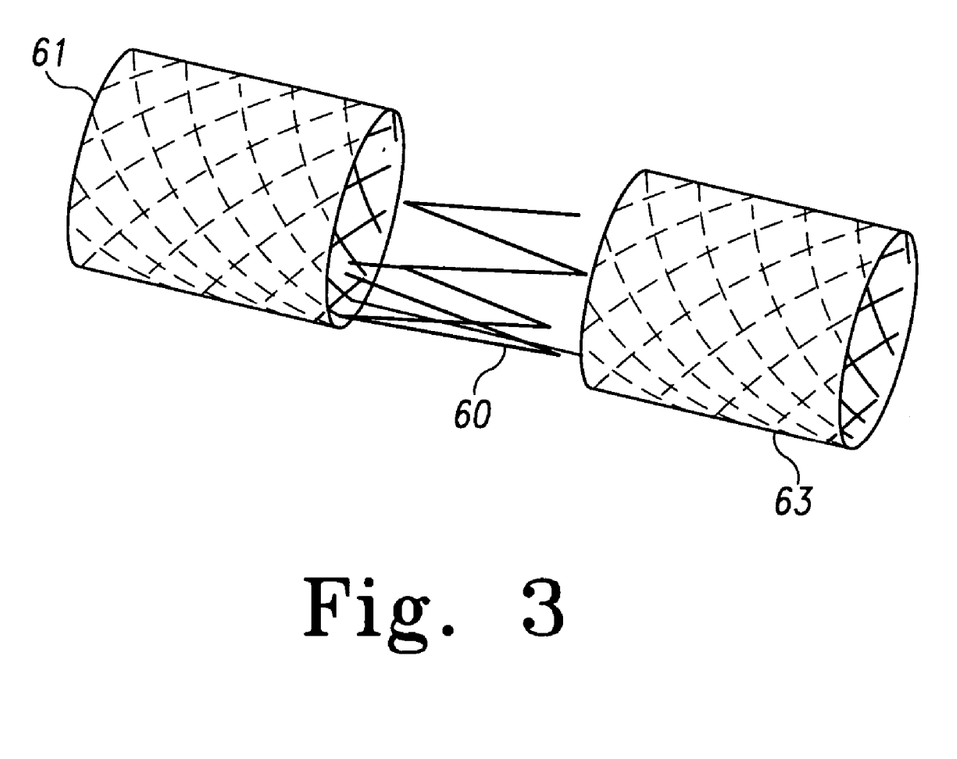
FIG. 3 shows a flexible bridge configured as a partial stent.

In another example, the flexible bridge includes a portion of one or more stents having a curved cross-section. Referring to FIG. 3, in a specific example the flexible bridge 60 is configured as a partial Z-stent, that is a Z-stent that has been cleaved at one point so as not to form an endless loop of stent material. This partial Z-stent bridge is irreversibly attached to stent portions of stent graft sections 61 and 63. Portions of a wide variety of stent materials and configurations may be used as partial stents for the flexible bridge. Such partial stents preferably have a curved cross-section.

Figure 4A:
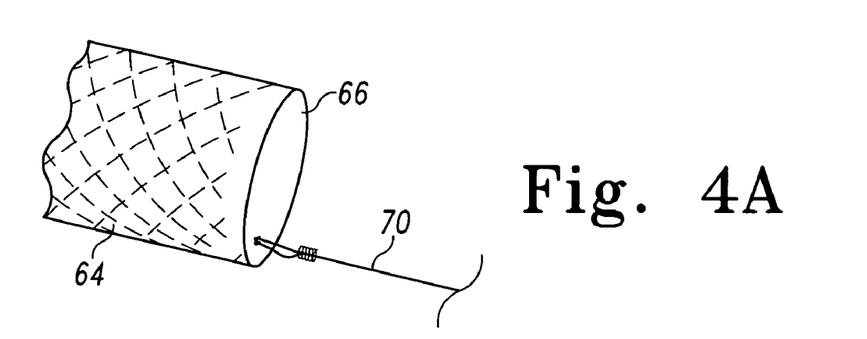
FIGS. 4A-4C show examples of irreversible attachments between a flexible bridge and stent graft sections.
Figure 4B:
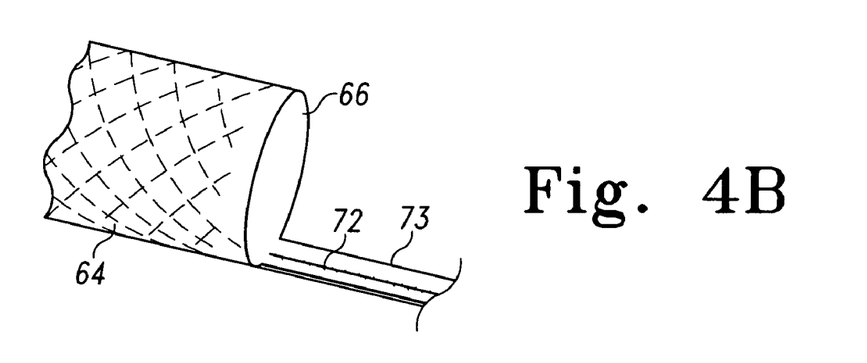
Figure 4C:
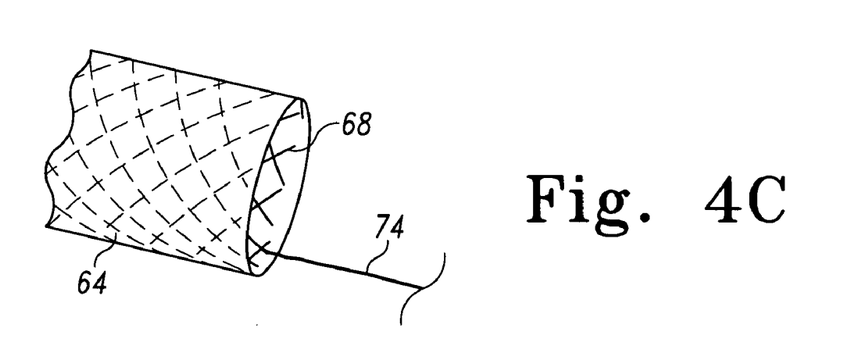

The flexible bridge is irreversibly attached to the stent graft sections, and can be attached to the graft material and/or to a stent of the stent graft section. The term "irreversible attachment" means that the flexible bridge cannot be separated from the stent graft section under a normal use environment without damaging or destroying either of the two components. A variety of irreversible attachments can be used. For example, the flexible bridge 70 can be irreversibly attached to the stent graft 64 by suturing an end of the bridge to the graft material 66 (FIG. 4A). In another example, the flexible bridge 72 can be irreversibly attached to the stent graft 64 by suturing the bridge to a length of graft material 73 that is irreversibly attached to the graft material 66 of the stent graft section (FIG. 4B). In yet another example, the flexible bridge 74 can be irreversibly attached to a stent 68 of the stent graft 64 (FIG. 4C). Preferably, the flexible bridge is attached to the stent of the stent graft section. The flexible bridge may be integral with one or both stents. That is, the flexible bridge and one or both stents may be formed from a single piece of material. The flexible bridge may be a separate piece of material that has been affixed to one or both stents by any of a variety of methods including welding, brazing, and soldering.

Preferably, the flexible bridge is a partial stent having a curved cross-section and irreversibly attached to each of the stents located at the central openings. Preferably the flexible bridge is made of a metal, such as stainless steel, nitinol, and other alloys. In a preferred configuration, the flexible bridge is a partial zig-zag stent and is integral with both of the stents located at the central openings, each of which are also zig-zag stents.

Figure 5A:
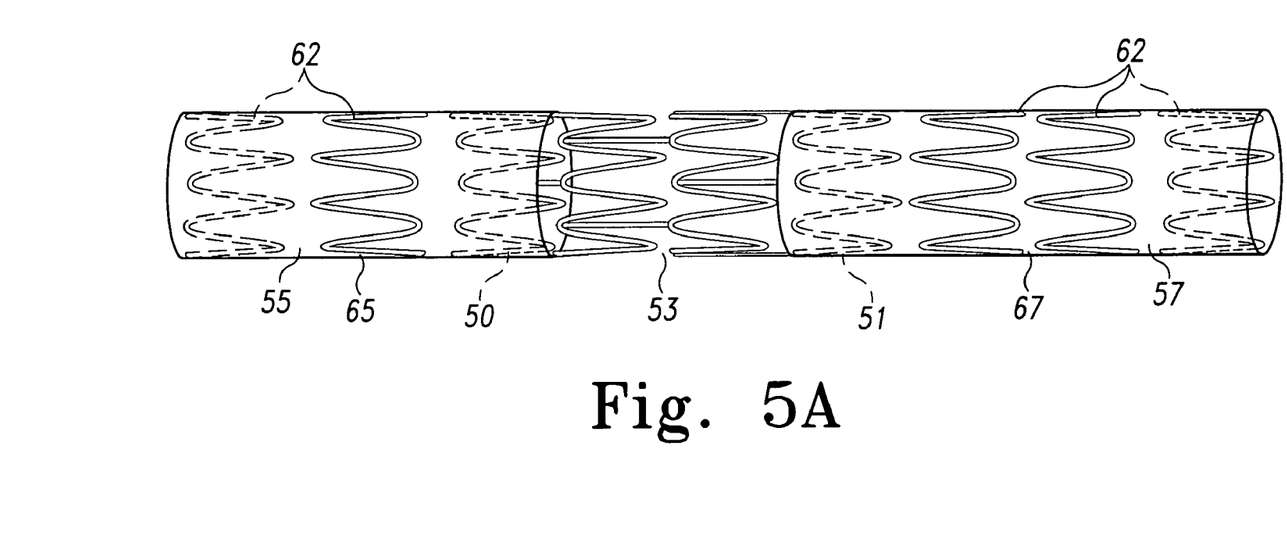
FIGS. 5A-5B show examples of interconnected leg extension prostheses having internal stents and a flexible bridge that are an integral portion of a connected zig-zag stent.
Figure 5B:
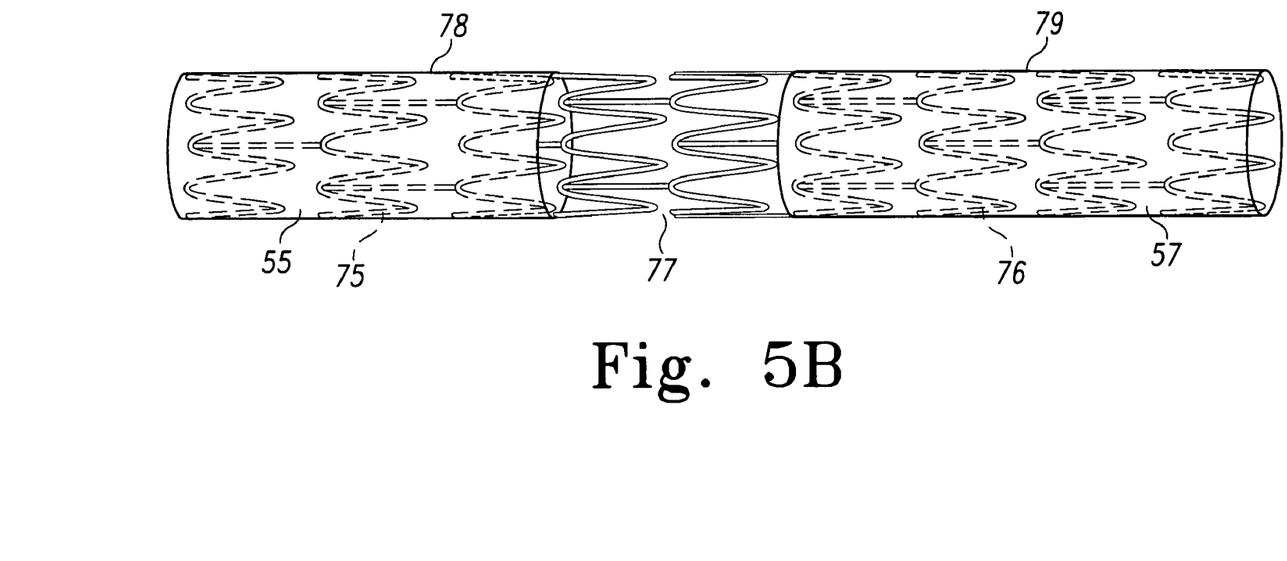

In another example, the flexible bridge is a partial stent that is a portion of a connected zig-zag stent. In this example, the flexible bridge is integral with each internal stent located at the central opening of each of the stent graft sections. Referring to FIG. 5A, internal stents 50 and 51 and the partial stent of the flexible bridge 53 are an integral portion of a single connected zig-zag stent. The internal stents are covered with graft material 55 and 57. The stent graft sections 65 and 67 may each have additional Z-stents 62 away from the central openings, and these stents may be internal or external. Referring to FIG. 5B, internal stents 75 and 76 are covered with graft material 55 and 57, and extend from the cental opening to the terminal opening of their respective stent graft sections 78 and 79. These internal stents and the partial stent of the flexible bridge 77 are an integral portion of a single connected zig-zag stent.

The dimensions of the flexible bridge and each of the stent graft sections are determined by the intended use of the prosthesis. Ideally, each section of the interconnected leg extension prosthesis, and each component of the prosthesis assembly of which the interconnected leg extension prosthesis is a component, is precisely constructed so as to provide the optimum fit of the prosthesis assembly with the vasculature to be treated. The dimensions of the vasculature may be determined by a variety of methods, including intraoperative intravascular ultrasound (IVUS) and radiologic studies such as computerized tomography (CT), magnetic resonance imaging (MRI), angiography. Interconnected prostheses may also be constructed so as to have a range of discrete sizes. In this way, the interconnected leg extension prosthesis can be kept in stock for use with other stock components for emergency treatments. This general type of system is described, for example in U.S. patent application Publication 2002/0198587 A1.

One of the possible uses of the interconnected leg extension prothesis is as a component of a prosthesis assembly for treatment of an aortic aneurysm. Such an assembly could include the interconnected leg extension prosthesis and a bifurcated prosthesis having a main tubular body with a proximal opening and two distal openings. The main tubular body of the bifurcated prosthesis is intended to attach to the healthy tissue above the aneurysm near the proximal opening of the prosthesis. The two openings at the distal end of the main tubular body form the bifurcation that fits over the iliac bifurcation such that each distal opening is at or within one of the iliac branch arteries. An example of such a bifurcated prosthesis is described in WO98/53761.

In the treatment of aortic aneurysms, the desired dimensions of an interconnected leg extension prosthesis are determined by the dimensions and condition (i.e. healthy or aneurysmal) of the iliac arteries and by the dimensions of the bifurcated prosthesis with which the leg extensions will coordinate. Referring again to FIG. 1, in this example the diameter 30 or 31 of a stent graft section will typically range from 8 mm to 24 mm, and the length 35 or 36 will typically range from 15 mm to 125 mm. The distance 38 between the central openings of the stent graft sections in this example will typically range from 30 mm to 60 mm. For a stent graft section containing two or more discrete stents or stent segments, the spacing 39 of the stents along the axis of the stent graft is preferably from 0 mm to 8 mm.

Figure 6:
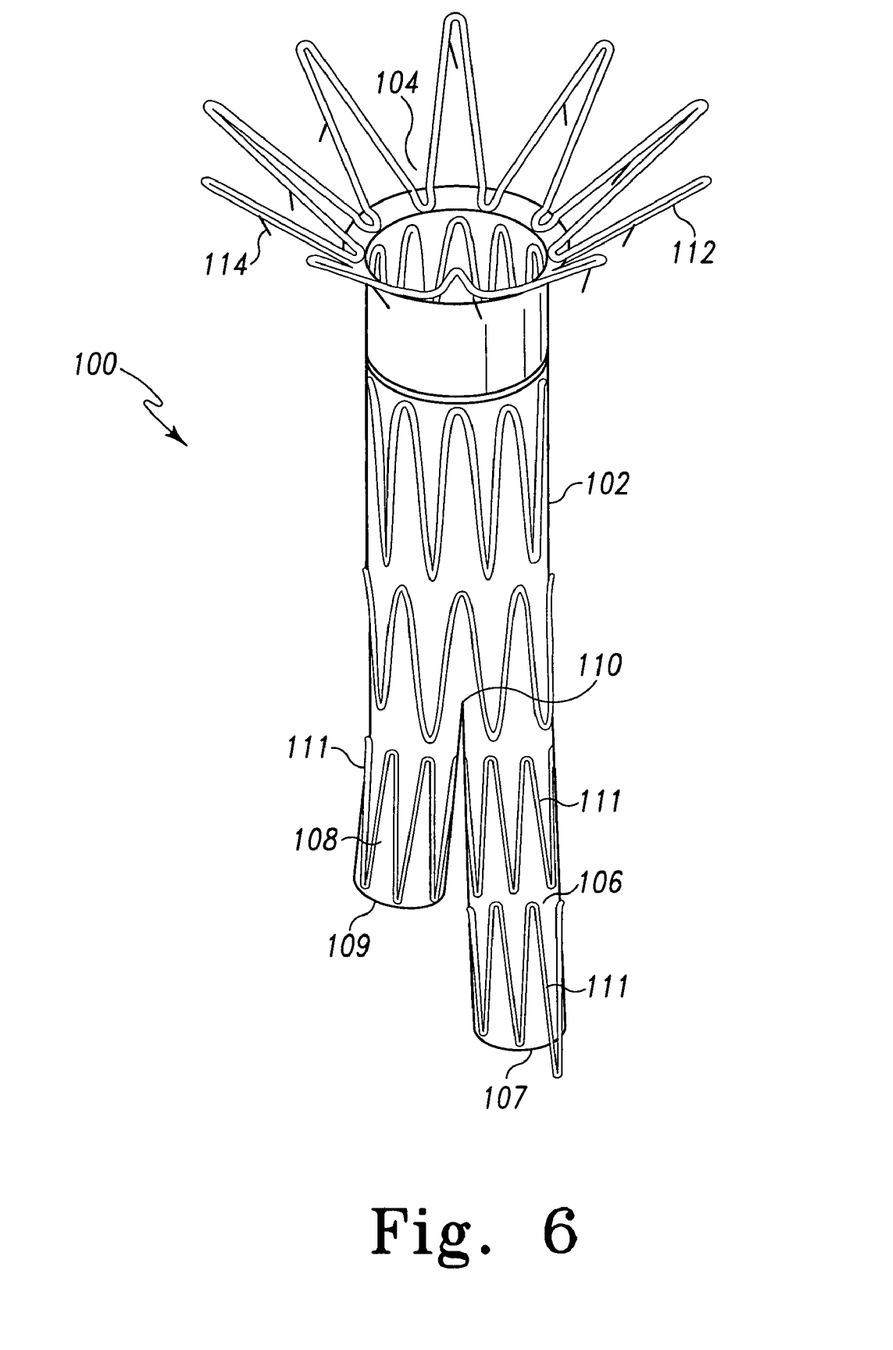
FIG. 6 shows a bifurcated prosthesis for treatment of aortic aneurysms.

One specific example of a bifurcated prosthesis for treatment of aortic aneurysms is the ZENITH™ AAA prosthesis system available from COOK, INC., which is generally described in WO98/53761. Referring to FIG. 6, this type of bifurcated prosthesis 100 has a main tubular body 102 with a proximal opening 104 and having two distal tubular legs 106 and 108 at the bifurcation 110. A stent 112 is attached to and extends from the graft material near the proximal opening 104. This stent contains barbs 114 to provide for anchoring of the prosthesis above the aneurysm. The longer distal leg 106 is typically deployed in the ipsilateral iliac artery, and the shorter distal leg 108 is typically deployed in the contralateral iliac artery. The shorter leg contains one external zig-zag stent 111 between the bifurcation and the distal opening 109, and the longer leg contains two external zig-zag stents 111 between the bifurcation and the distal opening 107.

Figure 7:
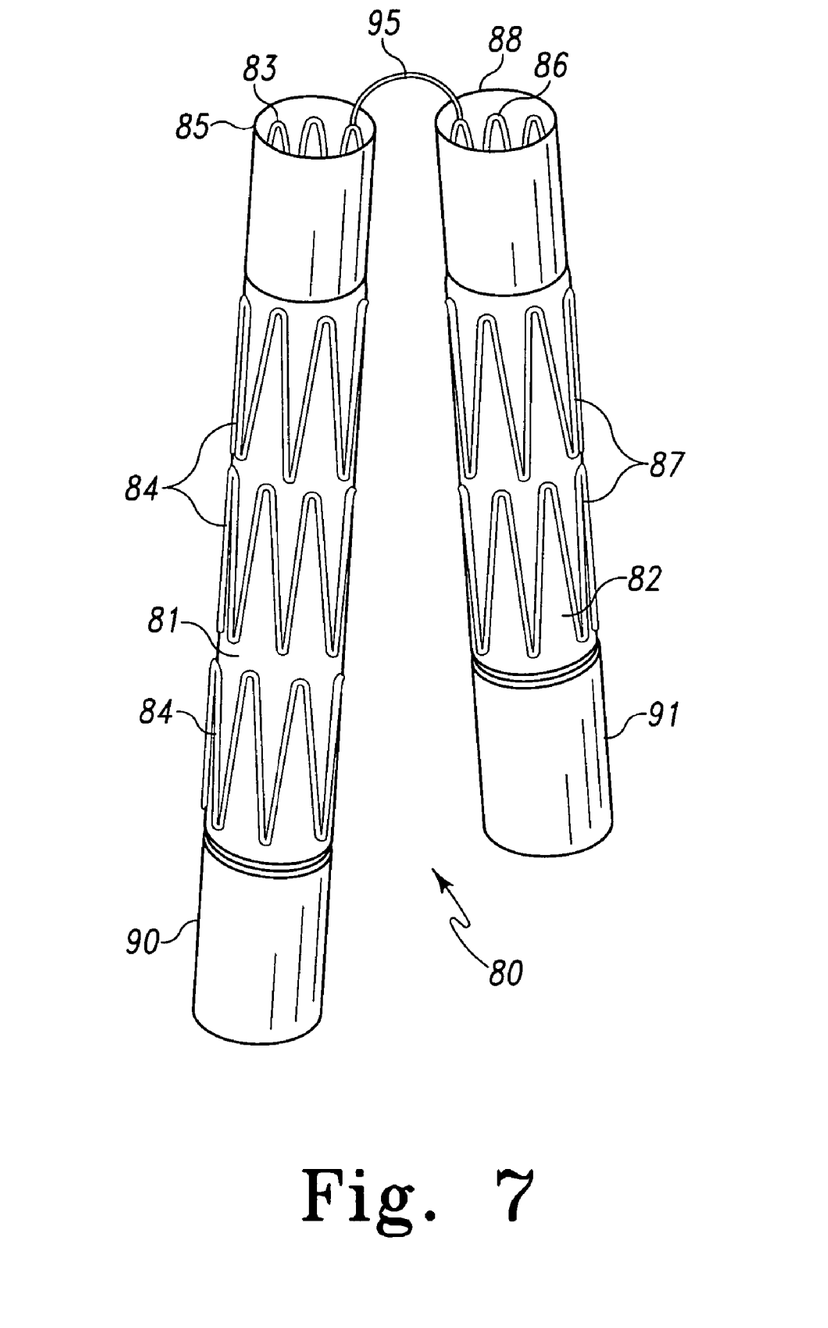
FIG. 7 shows an interconnected leg extension prosthesis for use with the bifurcated prosthesis of FIG. 6.

An example of an interconnected leg extension prosthesis 80 for use specifically with the bifurcated prosthesis of FIG. 6 is shown in FIG. 7. This example has a longer stent graft section 81 and a shorter stent graft section 82. These stent graft sections are designed to engage with the shorter and longer legs of the bifurcated prosthesis, respectively. The longer stent graft section contains an internal stent 83 near the central opening 85 and contains three external stents 84 along the length of the section. The shorter stent graft section contains an internal stent 86 near the central opening 88 and contains two external stents 87 along the length of the section. The terminal end 90 or 91 of each stent graft section can contain either an internal stent or an external stent. Internal stents are preferred for the terminal ends of the stent graft sections, as this may provide for enhanced sealing between the vessel wall and the prosthesis.

Referring still to FIG. 7, the flexible bridge 95 is shown in a bent form to illustrate a possible configuration of the prosthesis when deployed at the site of treatment. The flexible bridge is irreversibly attached to each of the internal stents at the central openings. When deployed, these central openings function as the proximal openings for each of the stent graft sections and are intended to coordinate with the distal openings of the bifurcated prosthesis.

Figure 8:
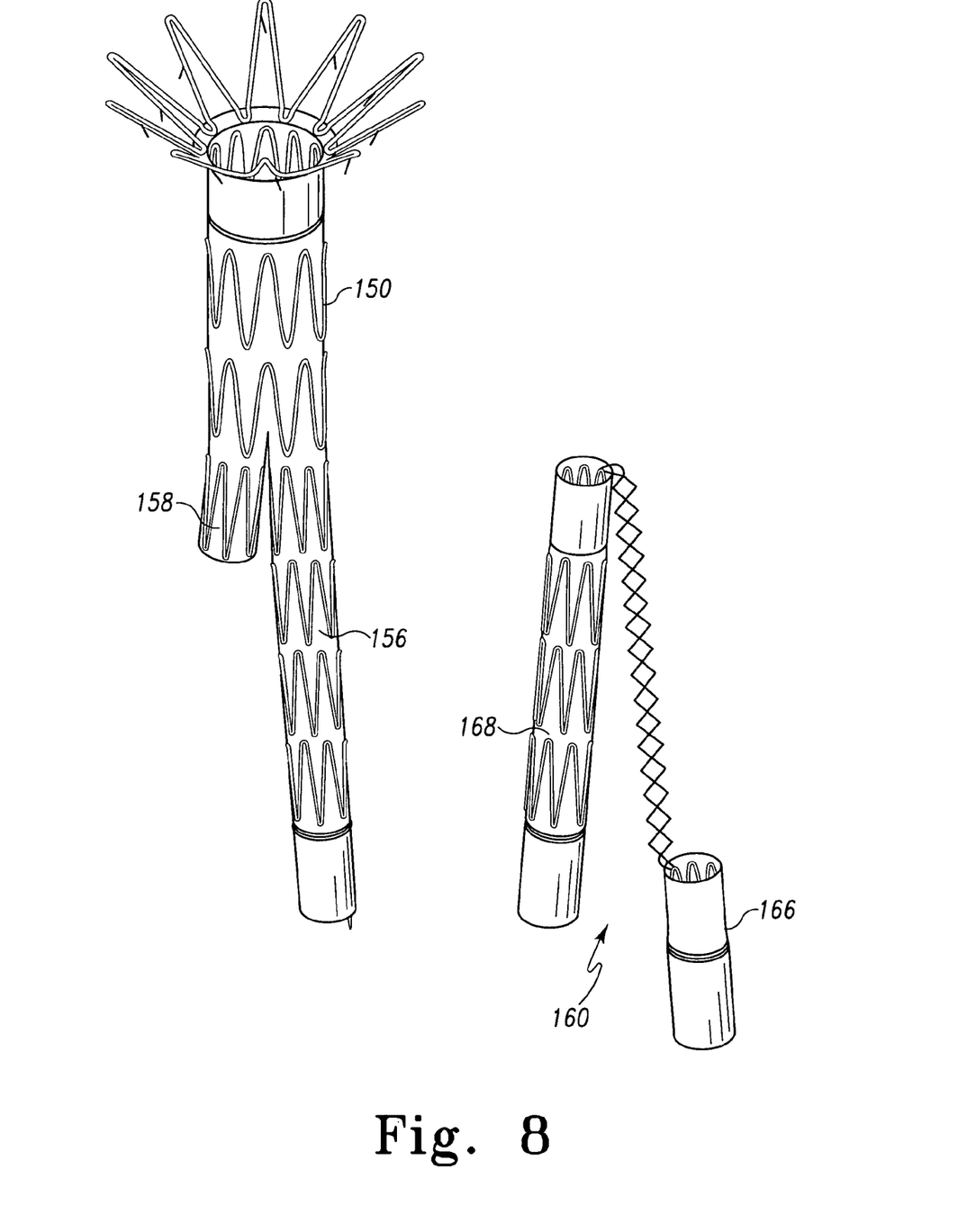
FIG. 8 shows an example of a prosthesis system with a bifurcated prosthesis and an interconnected leg extension prosthesis.

The length of the stent graft sections and the number of stents contained within the sections can vary independently. For example, referring to FIG. 8, a bifurcated prosthesis 150 has a longer distal leg 156 and a shorter distal leg 158. An interconnected leg extension prosthesis 160 for use with this bifurcated prosthesis can have a shorter stent graft section 166 and a longer stent graft section 168. Preferably the shorter stent graft section contains at least an internal stent at the central opening and another internal stent at the terminal opening. An interconnected leg extension prosthesis 80 as shown in FIG. 7 can also be used with bifurcated prosthesis 150, depending on the treatment requirements.

An interconnected leg extension prosthesis can be delivered to a treatment site using a variety of endovascular techniques. In treating aortic aneurysms, a catheter-based introducer can be used to insert a compressed prosthesis into the body through a femoral artery and then into the aorta. The introducer may be similar to those described in WO 03/53761 and in US2002/0198587.

Figure 9:
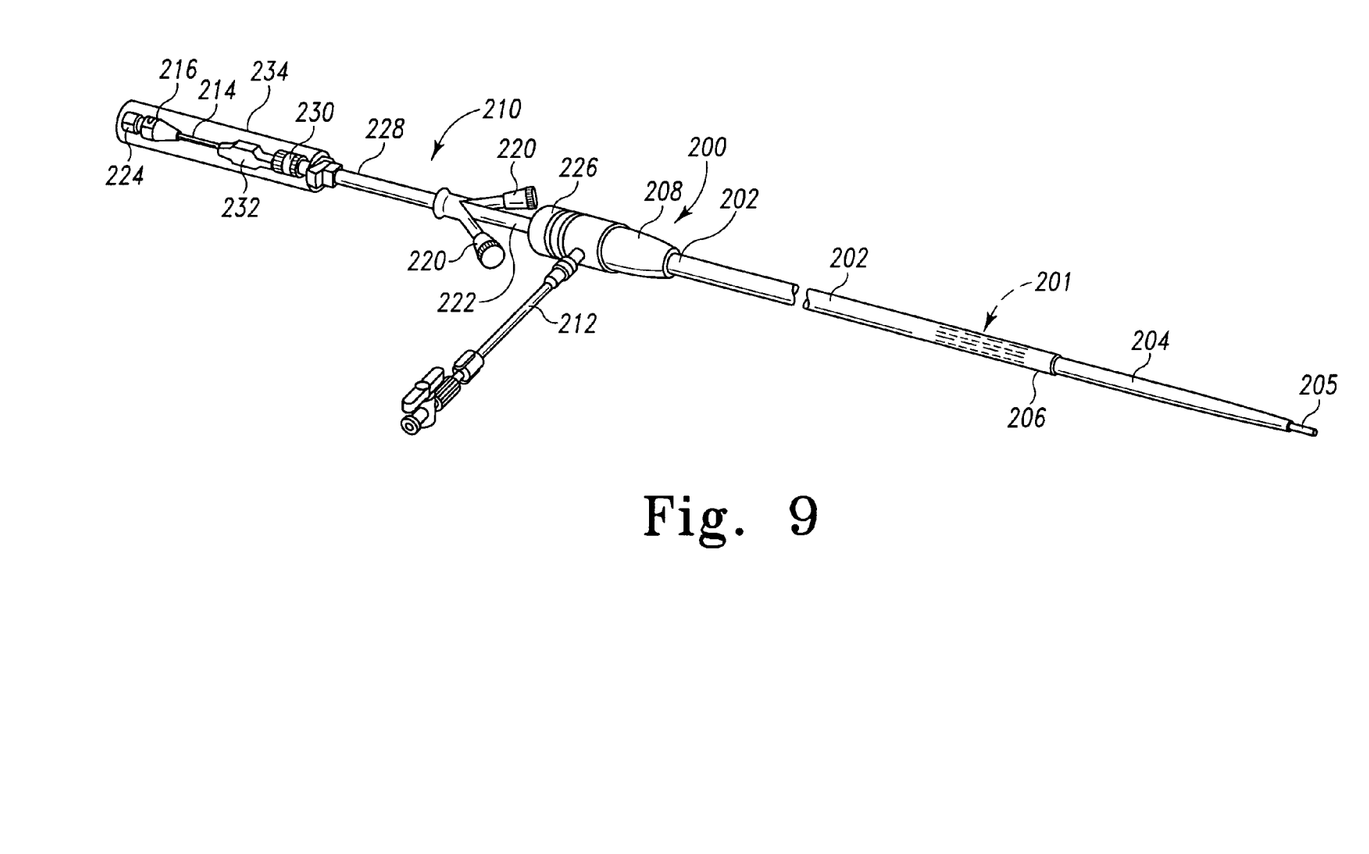
FIG. 9 shows an introducer for use with an interconnected leg extension prosthesis.

Referring to FIG. 9, an example of an introducer 200 for an interconnected leg extension prosthesis 201 includes a delivery sheath 202, tapered dilator 204 at proximal end 206, and a fitting 208 at distal end 210 of the delivery system. Inner cannula 214, which is connected to handle 216, extends completely from the tapered dilator 204 to distal end 210. Joined to the side of fitting 208 is an injection system 212, for saturating the prosthesis with anticoagulant heparin or other agents prior to deployment, and optionally for the injection of contrast medium or other agents after deployment.

Referring still to FIG. 9, the introducer 200 also includes check-flow valve 226, pusher 228, pusher fitting 230 and pin vise 232, all of which are covered with a protective tube 234. The protective tube 234 covers the distal end components during handling and is removed prior to use. Tabs 220 are provided at the distal end of short sheath 222, for peeling away the sheath prior to use. Sheath 222 protects the patency of the introducer lumen at the check-flow valve during shipping and handling, and extends only into fitting 208. Stylet 224 extends through cannula 214, through pusher 228 and introducer sheath 202 to a proximal tip 205 that protrudes from the proximal end of the tapered dilator 204. Stylet 224 is also of protective value during shipping and handling and is likewise removed prior to use in the medical procedure.

Figure 10:
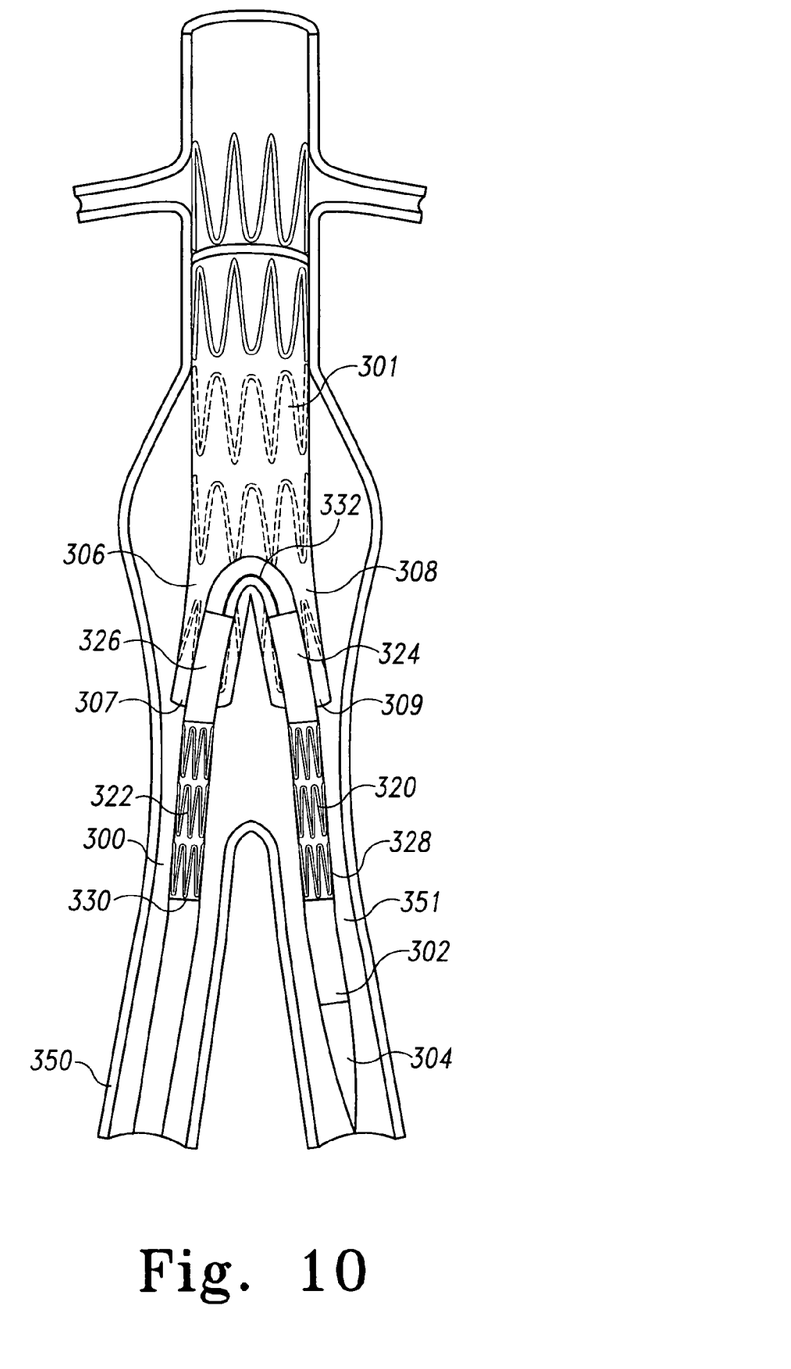
FIG. 10 shows an introducer containing an interconnected leg extension prosthesis during deployment within an aortic aneurysm.

Referring to the cutaway view of FIG. 10, delivery system 300 is introduced into the patient in delivery sheath 302 by insertion through ipsilateral iliac artery 350 and into the distal opening 307 of a bifurcated prosthesis 301 that has been deployed in the main aorta. The inner cannula is then bent at an acute angle to direct the dilator 304 down the contralateral artery 351 and past the other distal opening 309 of the bifurcated prosthesis. At this point, the compressed central opening 324 of stent graft section 320 is within the distal portion of leg 308, the compressed central opening 326 of stent graft section 322 is within distal portion of leg 306, and the flexible bridge 332 is bent at an acute angle. The delivery sheath 302 can then be pulled back towards the distal end of the delivery system, sequentially releasing the terminal opening 328 and the central opening 324 of stent graft section 320, the flexible bridge 332, and the central opening 326 and the terminal opening 330 of stent graft section 322.

Figure 11:
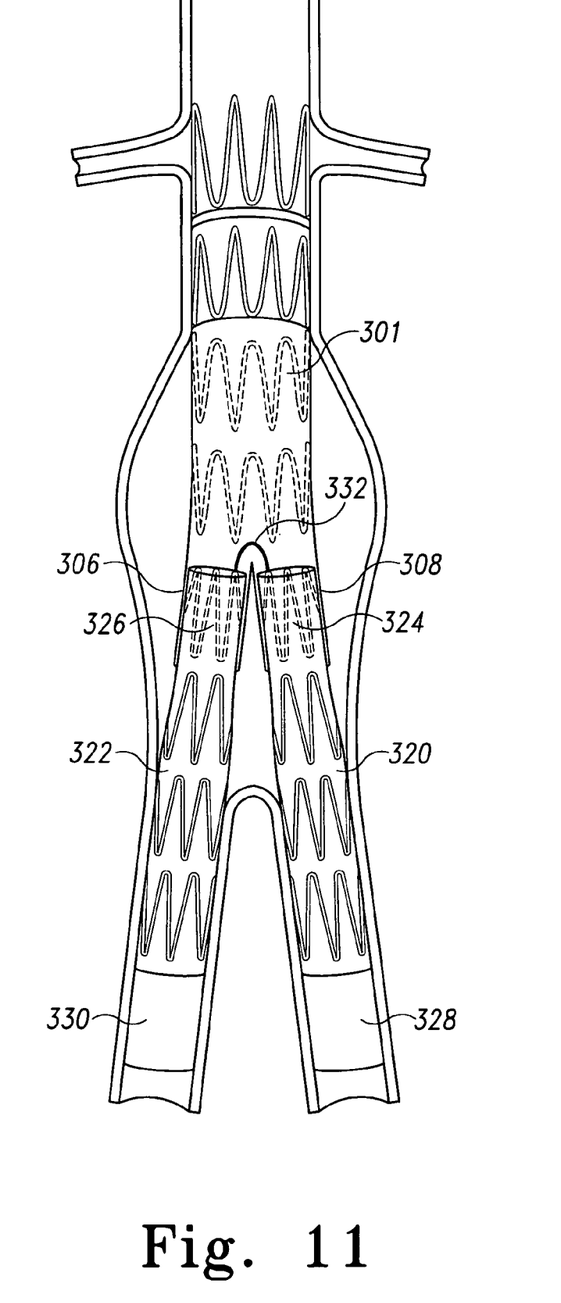
FIG. 11 shows a deployed prosthesis system with a bifurcated prosthesis deployed in the aorta and an interconnected leg extension prosthesis deployed into the iliac arteries.

Referring to FIG. 11, as each stent graft section of the prosthesis is released, that section self-expands and may press against the inner surface of the bifurcated prosthesis or against the vessel wall of the iliac artery. The central opening portions 324 and 326 expand against the distal portions of legs 306 and 308, establishing a friction fit between the stent graft sections and the bifurcated prosthesis. Thus, the stent graft sections 320 and 322 function as leg extensions for the prosthesis assembly, and central openings 324 and 326 function as the proximal ends of the legs. The terminal openings 328 and 330 engage the vessel wall in the iliac arteries and function as the distal ends of the legs. The attachment of the prosthesis at the implantation site and its sealing engagement to the bifurcated prosthesis and to the vessel walls may be further enhanced by inflating a molding balloon at each site to fully expand the prosthesis to press against the bifurcated prosthesis and/or the vessel wall.

As is evident from FIG. 11, the flexible bridge is bent over the bifurcation within the main prosthesis, and the graft material of each stent graft section overlaps with the graft material of the main prosthesis. Delivery of the complete prosthesis assembly is simplified since both leg extensions are part of a single interconnected component. In addition, this prosthesis system provides a reduced risk of leg extension separation due to the counterbalancing of forces on the two iliac leg stent grafts.

Throughout this specification various indications have been given as to the scope of the invention but the invention is not limited to any one of these but may reside at two more of these combined together. The examples are given for illustration only and not for limitation.

The invention claimed is:
1. A modular endoluminal prosthesis comprising:
 a primary prosthetic module comprising a graft and at least a first proximal opening and first and second distal openings defining a bifurcation; and
 a secondary prosthetic module comprising a first stent graft having a first graft and at least one stent, a second stent graft having a second graft and at least one stent, and a flexible bridge having a first end attached to the first stent graft and a second end attached to the second stent graft;
 where at least a portion of the first stent graft is disposed within and extends through the first distal opening of the primary prosthetic module and at least a portion of the second stent graft is disposed within and extends through the second distal opening of the primary prosthetic module; and
 where the bridge is longitudinally flexible and expands within the primary prosthetic module from a first configuration to a second configuration, where the distance along the bridge between the first and second stent grafts is greater in the second configuration than in the first configuration so that the combined length of the first stent graft, second stent graft, and bridge, is greater in the second configuration than in the first configuration, and where the bridge spans the bifurcation.

2. The prosthesis of claim 1 where the bridge comprises a zig-zag or sinusoidal shape undulating along a longitudinal path between the first and second ends.

3. The prosthesis of claim 1 where the length of the bridge between the first and second stent grafts is greater than the distance along the bridge between the first and second stent grafts.

4. The prosthesis of claim 1 where, in the second configuration, the first stent graft is disposed at an acute angle to the second stent graft.

5. The prosthesis of claim 1 where, in the second configuration, the bridge is bent into an acute angle.

6. The prosthesis of claim 1 where the flexible bridge comprises at least one wire having a first end attached to the first stent graft, a second end attached to the second stent graft, and a zigzag or sinusoidal shape undulating along a longitudinal path between the first and second ends.

7. The prosthesis of claim 1 where the first stent graft has a different length than the second stent graft.

8. The prosthesis of claim 1 where the primary prosthetic module comprises a first distal leg and a second distal leg and where the first stent graft extends the first distal leg of the primary prosthetic module and the second stent graft extends the second distal leg of the primary prosthetic module.

9. The prosthesis of claim 8 where the first leg is longer than the second leg and the second stent graft is longer than the first stent graft.

* * * * *